US011467240B2

(12) United States Patent
Yap et al.

(10) Patent No.: US 11,467,240 B2
(45) Date of Patent: Oct. 11, 2022

(54) METHODS, SYSTEMS, AND COMPUTER READABLE MEDIA FOR ACCELERATING DIFFUSION MAGNETIC RESONANCE IMAGING (MRI) ACQUISITION VIA SLICE-INTERLEAVED DIFFUSION ENCODING

(71) Applicant: The University of North Carolina at Chapel Hill, Chapel Hill, NC (US)

(72) Inventors: Pew-Thian Yap, Chapel Hill, NC (US); Yoonmi Hong, Chapel Hill, NC (US); Wei-Tang Chang, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 17/139,426

(22) Filed: Dec. 31, 2020

(65) Prior Publication Data

US 2021/0199743 A1 Jul. 1, 2021

Related U.S. Application Data

(60) Provisional application No. 62/955,997, filed on Dec. 31, 2019.

(51) Int. Cl.
*G01V 3/00* (2006.01)
*G01R 33/565* (2006.01)
(Continued)

(52) U.S. Cl.
CPC ........ *G01R 33/56545* (2013.01); *A61B 5/055* (2013.01); *G01R 33/4835* (2013.01);
(Continued)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

| 7,034,531 B1* | 4/2006 | Tuch | ................ G01R 33/56341 324/309 |
| 7,315,756 B2* | 1/2008 | Yarnykh | .............. G01R 33/563 600/411 |

(Continued)

FOREIGN PATENT DOCUMENTS

CN 112488975 A * 3/2021

OTHER PUBLICATIONS

Commonly-Assigned, co-pending U.S. Appl. No. 17/127,366 for "Methods, Systems, and Computer Readable Media for Using a Trained Adversarial Network for Performing Retrospective Magnetic Resonance Imaging (MRI) Artifact Correction," (Unpublished, filed Dec. 18, 2020).

(Continued)

*Primary Examiner* — Walter L Lindsay, Jr.
*Assistant Examiner* — Frederick Wenderoth
(74) *Attorney, Agent, or Firm* — Jenkins, Wilson, Taylor & Hunt, P.A.

(57) ABSTRACT

A method for accelerating diffusion magnetic resonance imaging (MRI) acquisition via slice interleaved diffusion encoding (SIDE) includes conducting a plurality of simultaneous multislice (SMS) excitations for each of a plurality of SIDE diffusion-weighted volumes to obtain SMS images of an MRI subject at different diffusion orientations, regrouping the images into slice groups with different orientations, generating a plurality of slice-undersampled diffusion weighted volumetric images of the subject, wherein each of the plurality of slice-undersampled diffusion (Continued)

weighted volumetric images is produced by cyclically interleaving the slice groups, such that each slice group is associated with a different diffusion wavevector, and reconstructing a full diffusion-weighted volumetric image of the subject by providing the plurality of slice-undersampled diffusion weighted volumetric images to a neural network trained to produce full diffusion-weighted volumetric versions of diffusion magnetic resonance images from undersampled versions of the diffusion magnetic resonance images.

20 Claims, 11 Drawing Sheets

(51) Int. Cl.
| | |
|---|---|
| *G06T 11/00* | (2006.01) |
| *G01R 33/483* | (2006.01) |
| *G06N 3/08* | (2006.01) |
| *A61B 5/055* | (2006.01) |
| *G01R 33/56* | (2006.01) |
| *A61B 5/00* | (2006.01) |

(52) U.S. Cl.
CPC ........... *G01R 33/5608* (2013.01); *G06N 3/08* (2013.01); *G06T 11/005* (2013.01); *G06T 11/006* (2013.01); *A61B 5/0042* (2013.01); *G06T 2210/41* (2013.01)

(58) Field of Classification Search
USPC .......................................................... 324/309
See application file for complete search history.

(56) References Cited

U.S. PATENT DOCUMENTS

| | | | | |
|---|---|---|---|---|
| 9,891,302 | B2* | 2/2018 | Topgaard | G01R 33/5608 |
| 2010/0128797 | A1* | 5/2010 | Dey | H04N 19/103 |
| | | | | 375/240.24 |
| 2011/0199084 | A1* | 8/2011 | Hasan | A61B 5/055 |
| | | | | 324/309 |
| 2014/0184224 | A1* | 7/2014 | Nevo | G06T 7/0012 |
| | | | | 324/318 |
| 2017/0010340 | A1* | 1/2017 | Eichner | G01R 33/288 |
| 2018/0049665 | A1* | 2/2018 | Jeong | A61B 5/055 |
| 2020/0111194 | A1 | 4/2020 | Wang et al. | |
| 2021/0082092 | A1 | 3/2021 | Sargent et al. | |
| 2021/0190892 | A1 | 6/2021 | Yap | |

OTHER PUBLICATIONS

Howell et al., "The UNC/UMN Baby Connectome Project (BCP): An overview of the study design and protocol development," NeuroImage, vol. 185, pp. 891-905 (2019).
"Generative adversarial network," Wikipedia, pp. 1-10 (Dec. 7, 2019).
"Neural Network," Wikipedia, pp. 1-10 (Nov. 12, 2019).
Kustner et al., "Retrospective correction of motion-affected MR images using deep learning frameworks," Magn Reson Med, vol. 82, pp. 1527-1540 (2019).
Tamada et al., "Motion Artifact Reduction Using a Convolutional Neural Network for Dynamic Contrast Enhanced MR Imaging of the Liver," Magn Reson Med Sci, vol. 19, pp. 64-76 (Apr. 26, 2019).
Pelxelro, "Hitchhiker's Guide to Residual Networks (ResNet) in Keras," https://towardsdatascience.com/hitchhikers-guide-to-residual-networks-resnet-in-keras-385ec01ec8ff, pp. 1-8 (Apr. 8, 2019).
Haskell et al., "Network Accelerated Motion Estimation and Reduction (NAMER): Convolutional neural network guided retrospective motion correction using a separable motion model," Magn Reson Med., pp. 1-10 (2019).
Johnson et al., "Conditional generative adversarial network for 3D rigid-body motion correction in MRI," Magn Reson Med., vol. 82, pp. 901-910 (2019).
Kumar, "Autoencoder: Downsampling and Upsampling," OpenGenus, pp. 1-7 (Feb. 15, 2019).
Duffy et al., "Retrospective correction of motion artifact affected structural MRI images using deep learning of simulated motion," 1st Conference on Medical Imaging with Deep Learning, pp. 1-8 (2018).
Johnson et al., "Motion correction in MRI using deep learning," In Proceedings of the 26th Annual Meeting ISMRM, pp. 1-2 (2018).
Isola et al., "Image-to-Image Translation with Conditional Adversarial Networks," arXiv:1611.07004v3 (Nov. 26, 2018).
Zhu et al., "Unpaired Image-to-Image Translation using Cycle-Consistent Adversarial Networks," arXiv:1703.10593v6, pp. 1-18 (Nov. 15, 2018).
Ulyanov et al., "Improved Texture Networks: Maximizing Quality and Diversity in Feed-forward Stylization and Texture Synthesis," arXiv:1701.02096v2, pp. 1-9 (Nov. 6, 2017).
Liu et al., "Unsupervised Image-to-Image Translation Networks," 31st Conference on Neural Information Processing Systems (NIPS 2017), pp. 1-9 (2017).
Jin et al., "Deep Convolutional Neural Network for Inverse Problems in Imaging," IEEE Transactions on Image Processing, vol. 26, No. 9, pp. 4509-4522 (Sep. 2017).
Mao et al., "Least Squares Generative Adversarial Networks," In Proceedings of the IEEE International Conference on Computer Vision (ICCV), pp. 2794-2802 (2017).
Zhu et al., "Toward Multimodal Image-to-Image Translation," 31st Conference on Neural Information Processing Systems (NIPS 2017), pp. 1-12 (2017).
Simonyan et al., "Very Deep Convolutional Networks for Large-Scale Image Recognition," arXiv:1409.1556v6, pp. 1-14 (Apr. 10, 2015).
Zaitsev et al., "Motion Artefacts in MRI: a Complex Problem with Many Partial Solutions," J Magn Reson Imaging, vol. 42, No. 4, pp. 1-30 (Oct. 2015).
Andre et al., "Toward Quantifying the Prevalence, Severity, and Cost Associated with Patient Motion During Clinical MR Examinations," J Am Coll Radiol, vol. 12, pp. 689-695 (2015).
Budde et al., "Ultra-high resolution imaging of the human brain using acquisition-weighted imaging at 9.4 T," NeuroImage, vol. 86, pp. 592-598 (2014).
Maclaren et al., "Prospective Motion Correction in Brain Imaging: A Review," Magnetic Resonance in Medicine, vol. 69, pp. 621-636 (2013).
Schulz et al., "An embedded optical tracking system for motion-corrected magnetic resonance imaging at 7T," Magn Reson Mater Phy, vol. 25, pp. 443-453 (2012).
Maclaren et al., "Measurement and Correction of Microscopic Head Motion during Magnetic Resonance Imaging of the Brain," PLoS ONE, vol. 7, No. 11, pp. 1-9 (2012).
Ooi et al., "Prospective Real-Time Correction for Arbitrary Head Motion Using Active Markers," Magn Reson Med., vol. 62, No. 4, pp. 1-23 (Oct. 2009).
Qin et al., "Prospective Head Movement Correction for High Resolution MRI using an In-bore Optical Tracking System," Magn Reson Med., vol. 62, No. 4, pp. 1-22 (Oct. 2009).
Vertinsky et al., "Performance of Propeller relative to standard FSE T2-weighted imaging in pediatric brain MRI,"Pediatr Radiol, vol. 39, pp. 1-10 (2009).
Sheikh et al., "Image Information and Visual Quality," IEEE Transactions on Image Processing, vol. 15, No. 2, pp. 430-444 (Feb. 2006).
Zhuo et al., "MR Artifacts, Safety, and Quality Control," RadioGraphics, vol. 26, pp. 275-297 (2006).
Zaitsev et al., "Magnetic resonance imaging of freely moving objects: Prospective real-time motion correction using an external optical motion tracking system," NeuroImage, vol. 31, pp. 1038-1050 (2006).
Wang et al., "Image Quality Assessment: From Error Visibility to Structural Similarity," IEEE Transactions on Image Processing, vol. 13, No. 4, pp. 1-14 (Apr. 2004).

(56) References Cited

OTHER PUBLICATIONS

Wang et al., "Mulit-Scale Structural Similarity for Image Quality Assessment," Proceedings of the 37th IEEE Asilomar Conference on Signals, Systems and Computers, pp. 1-5 (Nov. 9-12, 2003).
Smith, "Fast Robust Automated Brain Extraction," Human Brain Mapping, vol. 17, pp. 143-155 (2002).
Wang et al., "A Universal Image Quality Index," IEEE Signal Processing Letters, vol. XX, No. Y, pp. 1-4 (Mar. 2002).
Zhang et al., "Segmentation of Brain MR Images Through a Hidden Markov Random Field Model and the Expectation-Maximization Algorithm," IEEE Transactions on Medical Imaging, vol. 20, No. 1, pp. 45-57 (Jan. 2001).
Pipe, "Motion Correction With Propellier MRI: Application to Head Motion and Free-Breathing Cardiac Imaging," Magnetic Resonance in Medicine, vol. 42, pp. 1-7 (1999).
Perlin, "An Image Synthesizer," SIGGRAPH '85, vol. 19, No. 3, pp. 1-10 (Jul. 22-26, 1985).
Non-Final Office Action for U.S. Appl. No. 17/127,366 (dated Oct. 5, 2021).
Notice of Allowance for U.S. Appl. No. 17/127,366 (dated Feb. 4, 2022).

\* cited by examiner

METHODS, SYSTEMS, AND COMPUTER READABLE MEDIA FOR ACCELERATING DIFFUSION MAGNETIC RESONANCE IMAGING (MRI) ACQUISITION VIA SLICE-INTERLEAVED DIFFUSION ENCODING

PRIORITY CLAIM

The present application claims the benefit of U.S. Provisional Patent Application Ser. No. 62/955,997, filed Dec. 31, 2019, the disclosure of which is incorporated herein by reference in its entirety.

GOVERNMENT INTEREST

This invention was made with government support under Grant Numbers NS093842 and EB006733 awarded by the National Institutes of Health. The government has certain rights in the invention.

TECHNICAL FIELD

The subject matter described herein relates to diffusion magnetic resonance imaging (MRI) acquisition methods. More particularly, the subject matter described herein relates to the acceleration of diffusion MRI acquisition using slice-interleaved diffusion encoding (SIDE).

BACKGROUND

At present, diffusion MRI (dMRI) techniques typically require a lengthy acquisition time for probing water diffusion in various directions and scales. This is especially problematic in certain applications or measurements where the subject must remain relatively motionless in a scanner. This is particularly problematic in cases where imaging is required of pediatric subjects or other patients that cannot remain sufficiently still (e.g., Parkinson's disease) during the image capturing process. As such, any reduction in acquisition time that can be achieved will not only improve the accuracy or clarity of images obtained, but will also reduce the levels of discomfort or distress experienced by patients and/or subjects.

Accordingly, in light of these difficulties, there exists a need for improved methods, systems, and computer readable media for accelerating diffusion magnetic resonance imaging acquisition via slice interleaved diffusion encoding.

SUMMARY

The subject matter described herein relates to methods, systems, and computer readable media for accelerating diffusion MRI acquisition using slice-interleaved diffusion encoding. One exemplary method includes conducting a plurality of simultaneous multislice (SMS) excitations for each of a plurality of SIDE diffusion-weighted volumes to obtain SMS images of an MRI subject at different diffusion orientations, wherein each SMS excitation captures a plurality of slice images of the MRI subject at one of the different diffusion orientations and with different orientations. The method further includes generating a plurality of slice-undersampled diffusion weighted volumetric images of the subject, wherein each of the plurality of slice-undersampled diffusion weighted volumetric images is produced by cyclically interleaving the slice groups, such that each slice group is associated with a different diffusion wavevector and reconstructing full diffusion-weighted volumetric images of the subject by providing the plurality of slice-undersampled diffusion weighted volumetric images to a neural network trained to produce full diffusion-weighted volumetric versions of diffusion magnetic resonance images from undersampled versions of the diffusion magnetic resonance images.

An exemplary system for accelerating diffusion magnetic resonance imaging acquisition via slice interleaved diffusion encoding includes at least one computing platform including at least one processor and a diffusion MRI acquisition acceleration engine executable by the at least one processor for conducting a plurality of simultaneous multislice (SMS) excitations for each of a plurality of SIDE diffusion-weighted volumes to obtain SMS images of an MRI subject at different diffusion orientations, wherein each SMS excitation captures a plurality of slice images of the MRI subject at one of the different diffusion orientations and with different orientations. The system is further configured for generating a plurality of slice-undersampled diffusion weighted volumetric images of the subject, wherein each of the plurality of slice-undersampled diffusion weighted volumetric images is produced by cyclically interleaving the slice groups, such that each slice group is associated with a different diffusion wavevector and reconstructing full diffusion-weighted volumetric images of the subject by providing the plurality of slice-undersampled diffusion weighted volumetric images to a neural network trained to produce full diffusion-weighted volumetric versions of diffusion magnetic resonance images from undersampled versions of the diffusion magnetic resonance images.

The subject matter described herein may be implemented in hardware, software, firmware, or any combination thereof. As such, the terms "function" "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

Embodiments of the subject matter described herein will now be explained with reference to the accompanying drawings, wherein like reference numerals represent like parts, of which.

DETAILED DESCRIPTION

Figure 1:
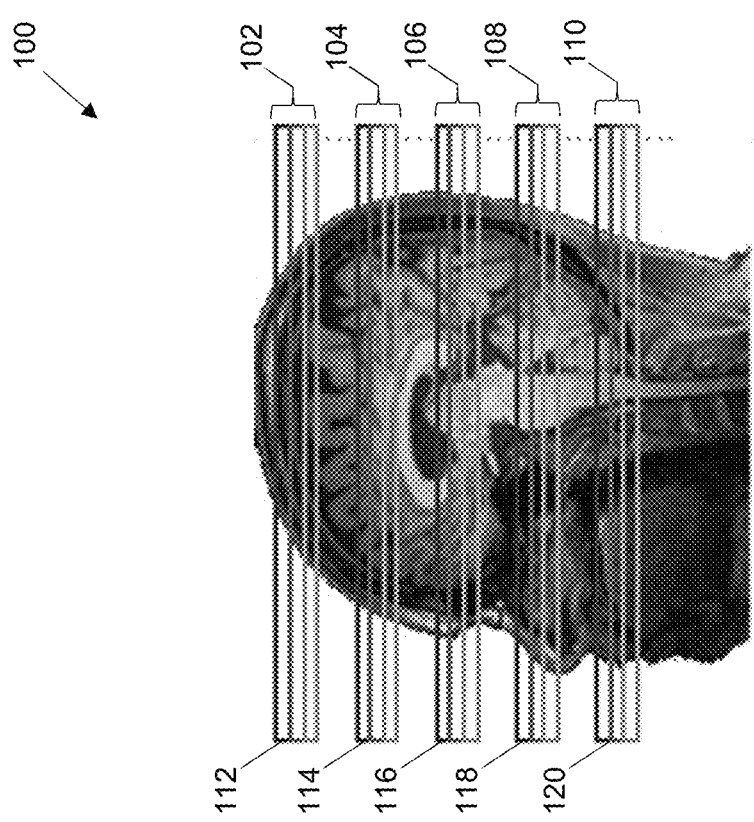
FIG. 1 is a diagram illustrating the simultaneous multi-slice (SMS) imaging of a head of a subject according to an embodiment of the subject matter described herein.

In accordance with the subject matter disclosed herein, methods, systems, and computer readable media for accelerating diffusion MRI (dMRI) acquisition using slice-interleaved diffusion encoding are provided. In some embodiments, the disclosed subject matter presents a system that, with multi-band imaging, accelerates dMRI acquisition by a significant amount (e.g., 50 times). In contrast to the usual approach of acquiring a full diffusion-weighted (DW) volumetric image for each diffusion wavevector, the disclosed systems and methods are configured to acquire a volumetric image comprising of interleaved slice groups for each repetition time (TR). Notably, each slice group corresponds to a different diffusion wavevector ("q"), which is also referenced as the 'diffusion sensitizing direction'. The resulting subsample of slices can then be utilized to generate and/or recover a full DW volumetric image of a subject (e.g., a patient's brain) using a graph convolutional neural network (GCNN). More specifically, the disclosed subject matter pertains to the acceleration of dMRI acquisition via slice-interleaved diffusion encoding (SIDE), such that only a subsample of slices (not an entire DW volume) are acquired for each diffusion wavevector. Accordingly, the disclosed system demonstrates that it is possible to reconstruct the full DW volumes from highly slice-undersampled volumes using a GCNN.

In some embodiments, dMRI is widely employed for studying brain tissue microstructure and white matter pathways. Notably, probing water molecules in a sufficient number of diffusion scales and directions is needed for a more specific quantification of tissue microenvironments and for a more accurate estimation of axonal orientations for tractography. This necessitates the acquisition of a large number of DW images and therefore increases acquisition time and susceptibility to motion artifacts, limiting the utility of dMRI for example to pediatric populations. A number of approaches have been proposed to reduce the acquisition time by undersampling either in q-space, or in both k-space and q-space. Consequently, reconstruction algorithms are typically designed for recovering the lost information in the undersampled data to reconstruct the DW images. Most algorithms recover lost information by assuming some kind of data regularity, such as smoothness, sparsity, and low-rank. Information recovery can also be achieved using deep learning, which typically learns a non-linear mapping from undersampled to fully-sampled data with the help of training image pairs. This in essence replaces handcrafted image assumptions with characteristics learned directly from the data. An example is the image quality transfer framework for reconstructing high-resolution images from their low-resolution counterparts using 3D convolutional neural networks (CNNs).

As indicated above, the disclosed subject matter presents a system and methodology to accelerate dMRI acquisition via SIDE, where each DW image volume is interleaved with slices encoded with multiple diffusion gradients. This technique is in contrast to conventional encoding schemes that typically encode each volume with a single diffusion gradient. SIDE can be seen as slice-undersampling with multiple diffusion gradients. SIDE differs from existing acceleration techniques in that SIDE does not seek to reduce the repetition time (TR) of a pulsed gradient spin echo (PGSE) echo planar imaging (EPI) experiment. Rather, SIDE is designed to acquire more incoherent information without reducing the TR. In particular, reducing the TR can have undesirable consequences such as lower SNR and increased spin-history artifacts.

In some embodiments, reconstructing the full DW volumes from the SIDE DW volumes can be done by first reorganizing the slices in the SIDE volumes to slice stacks according to the diffusion gradients. That is, each slice stack corresponds to a single diffusion gradient. The full DW volumes can then be recovered from the slice stacks with the help of regularity assumptions or image characteristics learned from the data. As described herein, the disclosed subject matter includes a reconstruction framework that is based on a graph convolutional neural network (GCNN), which extends CNNs to non-Cartesian domains represented by graphs. More specifically, the disclosed subject matter pertains to the acceleration of dMRI acquisition via SIDE, such that only a subsample of slices (not an entire DW volume) are acquired for each diffusion wavevector. Accordingly, the disclosed system demonstrates that it is possible to reconstruct the full DW volumes from highly slice-undersampled volumes using a GCNN.

In dMRI, a 3D image volume is acquired for each point in the diffusion wavevector space, i.e., q-space. While the voxels in each image volume reside on a uniform Cartesian grid, i.e., x-space, the points in q-space might not be distributed in a Cartesian manner. For example, it is common that sampling points are distributed on spherical shells. The GCNN uses a graph to capture the spatial relationships of points in both x-space and q-space so that the smoothness of the signal in the joint space can be used for effective reconstruction.

To improve the perceptual quality of DW image, the GCNN can be used as the generator in a generative adversarial network (GAN), which has demonstrated impressive results in natural image generation and in a variety of applications. The key contributor to the success of GANs is the use of an adversarial loss that forces the generated images to be indistinguishable from real images. This is implemented using a discriminator that learns a trainable loss function.

As previously mentioned, one aspect of the disclosed subject matter pertains to the SIDE acquisition technique. In particular, fully sampled DW images are reconstructed from SIDE volumes by learning a non-linear mapping based on a GCNN. The graph convolutional operation in the GCNN and is based on fast localized spectral filtering. In some embodiments, undersampling can be applied to an arbitrary scan direction (e.g., axial, coronal, and sagittal). For purposes of illustration and clarification, the disclosed subject matter as described herein utilizes axial acquisition. It should also be noted that in typical PGSE-EPI, the total acquisition time is proportional to the sequence TR and the number of wavevectors. Notably, the acquisition time is accelerated using the SIDE scheme, where only a subset of slices are required for each diffusion wavevector.

FIG. 1 is a diagram illustrating the simultaneous multi-slice (SMS) imaging of a head of a subject according to an embodiment of the subject matter described herein. Notably, the SIDE acquisition scheme depicted in FIG. 1 illustrates the use of SMS imaging with a factor of 5. For example, each SMS excitation is targeted at a slice group of 5 slices. As shown in FIG. 1, five slices 102-110 are depicted. Notably, grouping a slice element from each of the slices can be used to formulate a slice group. For example, the 5 slice elements 112-120 (i.e., the first slice element from each of the 5 slices depicted in FIG. 1) can be used to form a first slice group "SG #1". A second slice group ("SG #2") and third slice group ("SG #3") can be similarly formed by taking slice elements from each of slices 102-110 in a similar manner as the first slice group.

Figure 2:
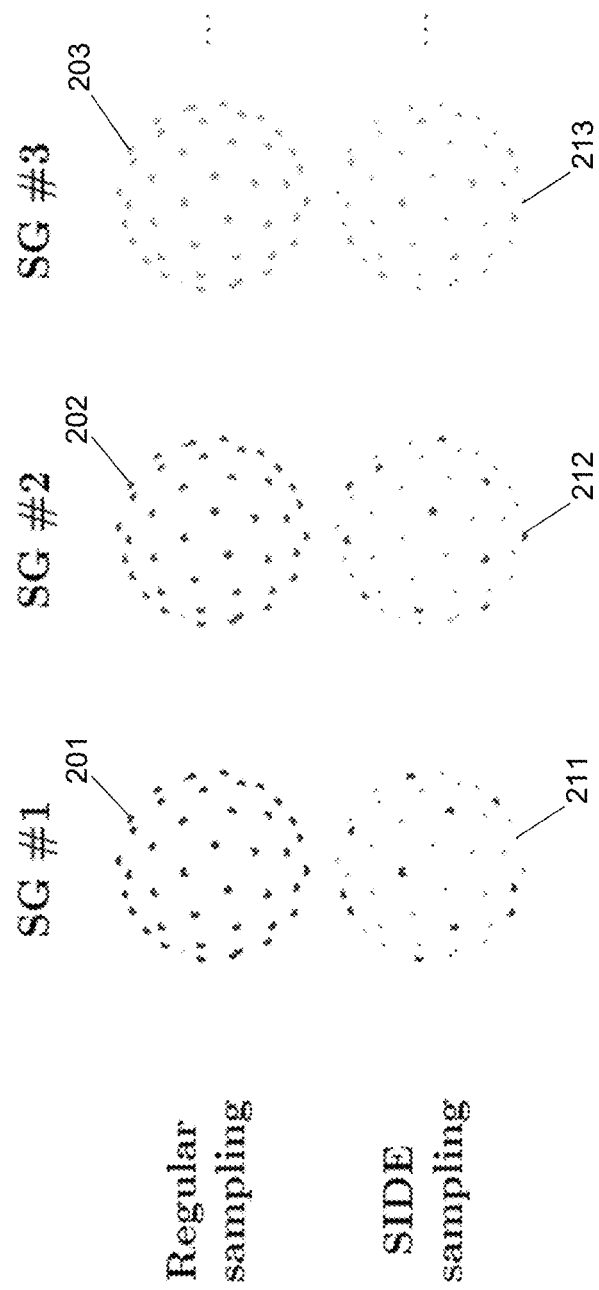
FIG. 2 is a diagram illustrating samplings in diffusion wavevector space with different slice groups according to an embodiment of the subject matter described herein.

FIG. 2 is a diagram illustrating samplings in diffusion wavevector space with different slice groups according to an embodiment of the subject matter described herein. In conventional dMRI acquisition, all of the slice groups in a volumetric image share the same diffusion encoding. This is depicted in the regular sampling examples 201-203 in the top row of FIG. 2. In contrast, SIDE acquisition as disclosed herein allows for each slice group to be associated with a different diffusion encoding. For example, SIDE acquisition permits the diffusion encodings of slice groups in a volumetric image to differ as shown in the SIDE sampling examples 211-213 depicted in the bottom row of FIG. 2.

Figure 3:
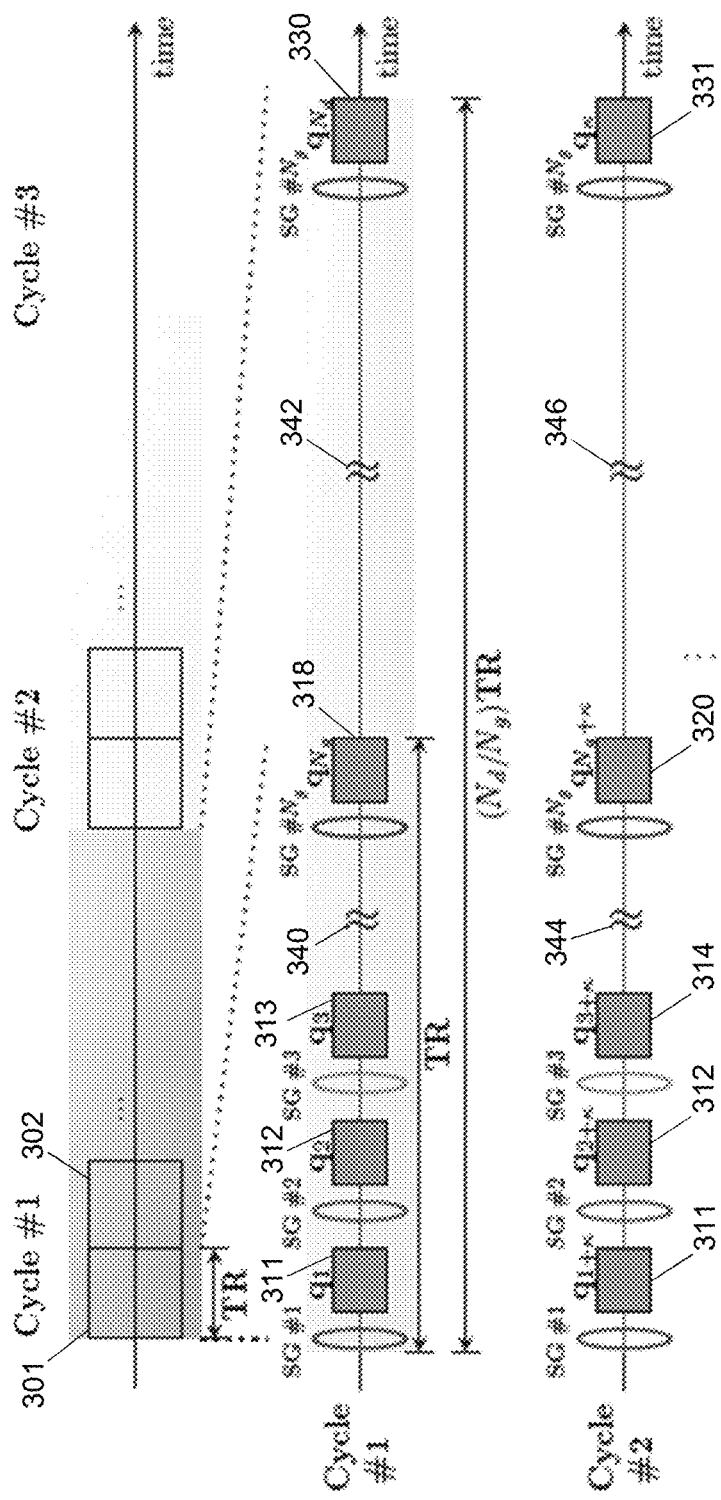
FIG. 3 is a diagram illustrating an exemplary slice-interleaved diffusion encoding (SIDE) sequence according to an embodiment of the subject matter described herein.

FIG. 3 is a diagram illustrating an exemplary SIDE acquisition sequence. Specifically, FIG. 3 illustrates that, in SIDE, the first SMS excitation is followed by the spin-echo EPI (SE-EPI) readout block 311 with the first diffusion wavevector $q_1$ in the gradient table. In some embodiments, the gradient table contains information on the diffusion sensitization gradients or, equivalently, wavevectors, usually in the form of diffusion weightings (i.e., b-values) and gradient directions (i.e., b-vectors). Notably, the (gray) SE-EPI readout block (e.g., block 311) is subjected to monopolar diffusion encoding in a TR period.

Moreover, the second slice group is encoded by the second diffusion wavevector $q_2$ (e.g., block 312), the third slice group is encoded by the third diffusion wavevector $q_3$ (e.g., block 313) and so on. In addition, variable $N_g$ depicted in FIG. 3 is defined to denote the number of slice groups in a volumetric image while $N_d$ is defined to represent the number of diffusion wavevectors (e.g., the number of diffusion directions). In some embodiments, $N_d$ can be assumed to be a multiple of $N_g$. In such scenarios, the first cycle of diffusion encoding will complete after $N_d/N_g$ TRs (e.g., as shown in the middle row of FIG. 3). In the next cycle, the gradient table and/or direction can be offset by kappa, K, where K is equal to any integer number (e.g., '1' or any other integer number that represents the gradient offset for each cycle) so that the first slice group in this "Cycle #2" is encoded by the $(1+K)^{th}$ gradient direction $q_{1+K}$ (i.e., a second gradient direction) as shown in the bottom row of FIG. 3 (see block 321). Notably, $N_g$ cycles cover all of the slices of all the diffusion wavevectors. In some embodiments, a subset of τ cycles can be selectively acquired for an acceleration factor of $R=N_g/T$.

The wavevector q depends on the length, strength, and orientation of the gradient pulses during the measurement sequence and the diffusion time on the pulse length and separation. For PGSE measurements, for example, $q=\gamma\delta G$ and $t=\Delta-(\delta/3)$ where γ is the gyromagnetic ratio, G is the diffusion gradient, t is the diffusion time, Δ is the time between the onsets of the two pulses, and both pulses have a length δ. Often q can be separated into scaler wave number |q| and a diffusion encoding direction $\hat{q}=q/|q|$, which is the direction of the magnetic field gradient in the diffusion-weighted pulses. The b-value summarizes both diffusion time and wave number $b=t|q|^2$. For spherical acquisition schemes, both t and |q| are fixed (so b is fixed) and only the gradient direction varies among measurements. The wavevectors can be computed from the b values and the gradient directions listed in the gradient table if the diffusion time is known.

Further, the ellipses 340-346 in the middle and bottom rows represent the SMS excitations. It is also note that the different colors (e.g., red, green, orange, blue, etc.) depicted in FIG. 3 indicate different slice groups. In some embodiments, a subset of the cycles, τ, can be selectively acquired based on a certain acceleration factor, $R=(N^g/\tau)$.

Figure 4:
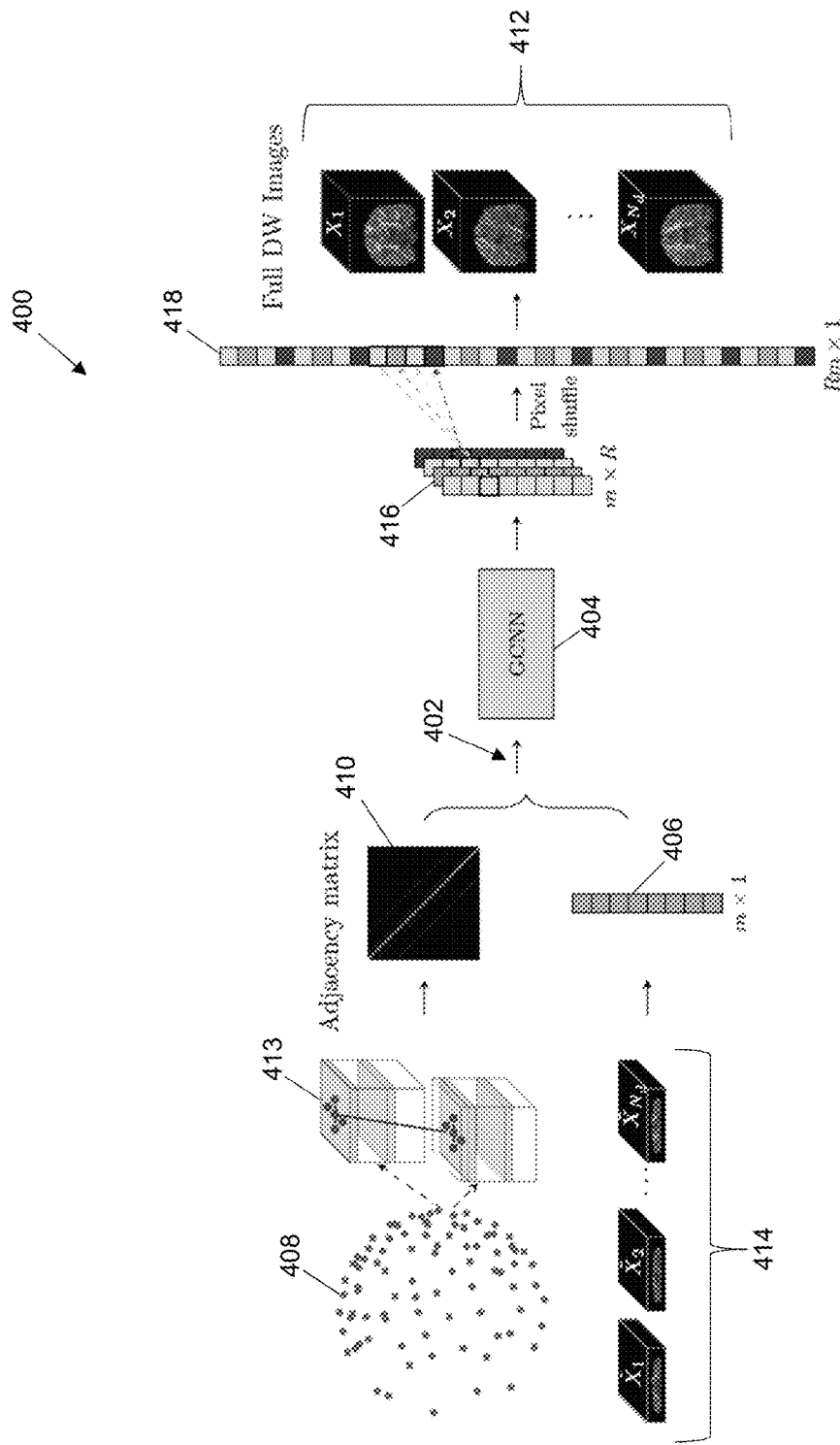
FIG. 4 is a diagram of an example graph convolutional neural network (GCNN)-based reconstruction framework according to an embodiment of the subject matter described herein.

In some embodiments, an exemplary reconstruction method that is conducted by a GCNN-based reconstruction framework is illustrated in FIG. 4. For each $n=1, \ldots, N_d$, let $\tilde{X}_n$ represent the slice stacks reorganized from the SIDE volumes acquired with a factor of R in the slice-select direction. One objective shown in FIG. 4 is to reconstruct the full DW volumes $\{X_n\}$ 412 from the undersampled DW volumes $\{\tilde{X}_n\}$ 414 by learning a non-linear mapping function $f$ such that $$(X_1, \ldots X_{N_d})=f(\tilde{X}_1, \ldots \tilde{X}_{N_d})$$

where $\{X_1, \ldots, X_{N_d}\}$ can be acquired after $N_g$ cycles. Further, $\{\tilde{X}_1, \ldots, \tilde{X}_{N_d}\}$ can be designated to represent subsampled DW images, which are rearranged from the SIDE multi-wavevector volumes. As indicated above, note that each $\tilde{X}_n$ is slice-undersampled by a factor of R.

Instead of reconstructing each DW volume individually, all DW volumes will be simultaneously reconstructed by jointly considering x-space and q-space neighborhoods. In some embodiments, the non-linear mapping function $f$ in the previous equation is learned using a GCNN 404. By joint consideration of x-space and q-space neighborhoods, the complementary information acquired from different DW volumes 414 can be harnessed jointly for effective reconstruction. Note that the input 402 of the GCNN 404 is a graph 406 constructed from the subsampled DW images (i.e., DW volumes 414) instead of the fully interpolated images. Input 402 further includes an adjacency matrix 410. The adjacency matrix 410 can be computed by jointly considering spatio-angular neighborhoods 413. Notably, the process illustrated in FIG. 4 reduces computational complexity and memory requirements.

In some embodiments, the dMRI signal is represented as a function defined on the nodes of a graph, where each node is determined by a physical spatial location in x-space and a wavevector in q-space. This graph is encoded with a weighted adjacency matrix W, which characterizes the relationships between two nodes. The graph Laplacian operator, defined as L=D−W with D being a diagonal degree matrix, plays an important role in graph signal processing. L can be normalized as $L_{I-D} := -1/2 WD^{-1/2}$ where I is an identity matrix. As L is real symmetric positive semidefinite, it has a set of orthonormal eigenvectors. The eigenvectors of L define the graph Fourier transform that enables the formulation of filtering in the spectral domain. Construction of the adjacency matrix W will be explained below.

In some embodiments, the disclosed subject matter utilizes spectral graph convolution. For example, localized graph filters can be defined based on spectral graph theory. According to Parseval's theorem, the spatial localization of the convolution corresponds to the smoothness in the spectral domain. Hence, localized filters can be approximated and parameterized by polynomials. Spectral filters represented by the K-th order polynomials of the Laplacian are K-hop localized in the graph. In some embodiments, a Chebyshev polynomial approximation can be employed to define the graph convolutional operation from input x to output y as $$y = g_\theta(x) = \sum_{k=0}^{K} \theta_k T_k(\tilde{L}) x$$

where $T_k(\tilde{L})$ is the Chebyshev polynomial of order k evaluated for the scaled Laplacian $\tilde{L} := 2L/\lambda_{max} - I$ with $\lambda_{max}$ being the maximal eigenvalue of L. Chebyshev polynomials $\{T_k(\cdot)\}$ form an orthogonal basis on $[-1,1]$ and can be computed by the stable recurrence relation $$T_k(\lambda) = 2\lambda T_{k-1}(\lambda) - T_{k-2}(\lambda), \text{ with } T_0(\lambda)=1, T_1(\lambda)=\lambda$$

Then, the graph convolutional layers in the GCNN can be represented as $$\Phi^{(l)} = \xi\left(\sum_{k=0}^{K} \Theta_k^{(l)} T_k(\tilde{L}) \Phi^{(l-1)}\right)$$

where $\Phi^{(l)}$ denotes the feature map at the l-th layer, $\theta_k^{(l)}$ is a matrix of Chebyshev polynomial coefficients to be learned at the l-th layer, and $\xi$ denotes a non-linear activation function.

In some embodiments, an adjacency matrix can also be used as input, For example, an adjacency matrix can be defined by jointly considering spatio-angular neighborhoods. The dMRI signal sampling domain can be represented as a graph with each node representing a spatial location $x_j \in \mathbb{R}^3$ and a normalized wavevector $\hat{q}_j \in \mathbb{S}^2$. Inspired by the x-q space neighborhood matching strategy for dMRI denoising, a symmetric adjacency matrix W with weight elements $\{w_{i,j,i',j'}\}$ is defined as:

$$w_{i,j,i',j'} := \exp\left(-\frac{\|x_i - x_{i'}\|_2^2}{\sigma_x^2}\right) \exp\left(-\frac{1 - \langle \hat{q}_j, \hat{q}_r \rangle^2}{\sigma_q^2}\right)$$

where $\pi_x$ and $\pi_q$ are the parameters used to control the contributions from the spatial and angular neighborhoods distances, respectively. It is noted that the numerators of the arguments of the exponential functions in the immediately preceding weight element equation are normalized to [0, 1].

Figure 5:
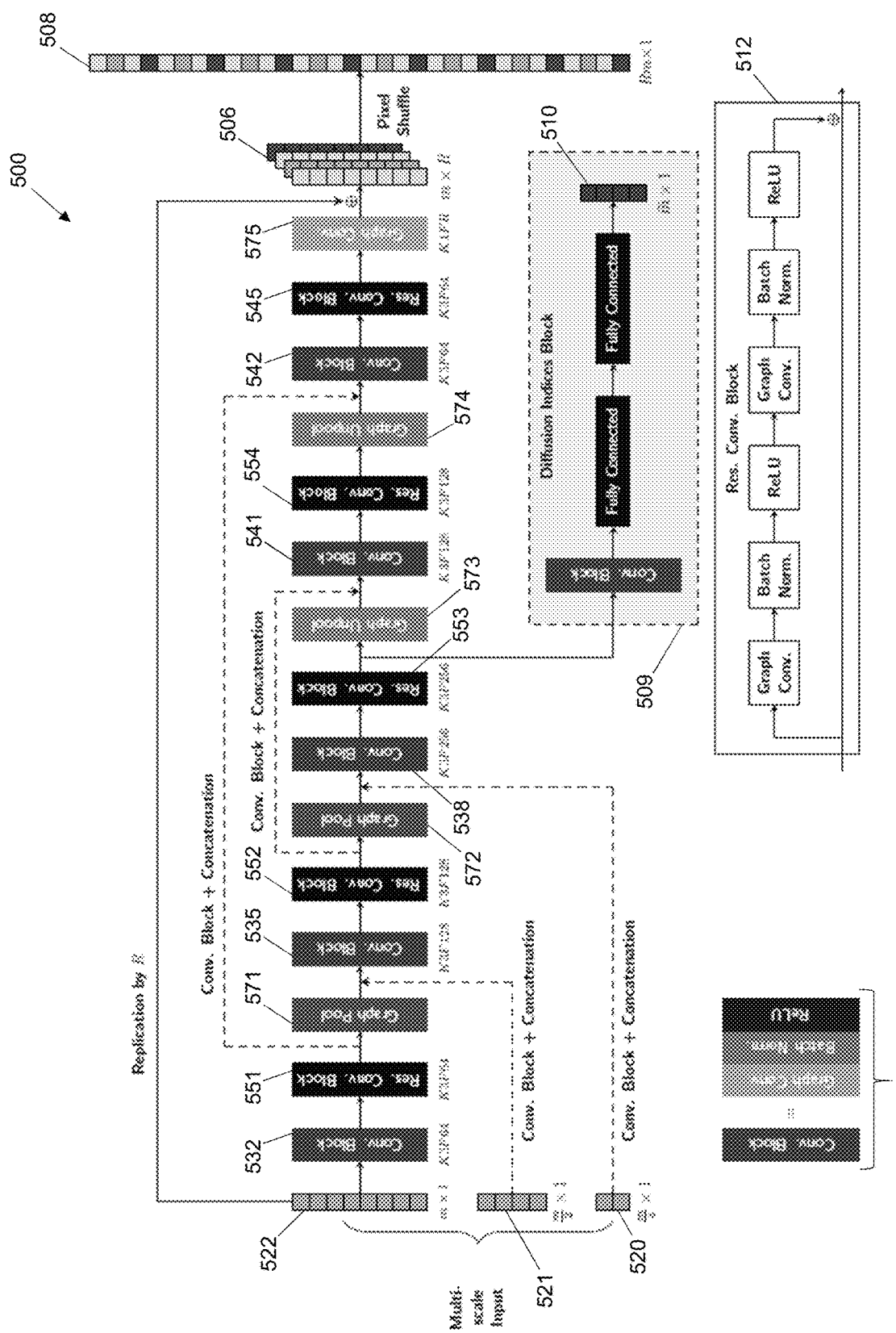
FIG. 5 is a diagram illustrating an exemplary logical graph convolutional neural network (GCNN) architecture according to an embodiment of the subject matter described herein.

In some embodiments, the disclosed subject matter utilizes a GCNN (e.g., as shown in FIG. 5). For example, the disclosed generator architecture can be based on U-Net with symmetric encoding and decoding paths. In U-Net, encoding and decoding pathways require pooling and unpooling operations, respectively. Graph coarsening and uncoarsening, which correspond to pooling and unpooling in standard CNNs, are not defined as straightforwardly. For graph coarsening, the Graclus multi-scale clustering algorithm can be utilized in some embodiments. Moreover, a residual convolutional block can be employed to ease network training since it can mitigate the problem of vanishing gradients. The graph signal can be represented as a single-array vector with permutation indices for rearrangement. The uncoarsening operation may be achieved via one-dimensional upsampling operation with a transposed convolution filter.

In some embodiments, multi-scale input graphs, generated from graph coarsening, can be added as new features with graph convolutions at the encoding path of each level. For skip connection for each level of the encoding path to the decoding path, a transformation module can be applied to boost the low-level features to complement the high-level features. Graph convolutions followed by concatenation in the transformation module narrow the gap between low and high-level features.

In some examples, the upsampling operation in the slice-select direction can be realized by standard convolutional layers in the low-resolution space followed by pixel shuffling in the last layer of the network as shown in FIG. 5. For example, the pixel-shuffling operation converts R pre-shuffled feature maps 506 of size m×1 to an output feature map 508 of size Rm×1, where m is the number of input graph nodes and R is the upsampling factor. In addition to the reconstruction of full DW images, a branch can be added in the decoding path to compute diffusion indices (e.g., see block 509) such as generalized fractional anisotropy (GFA). This branch can help the generator (e.g., GCNN 500) to produce dMRI data with more accurate diffusion indices. As an example, the present disclosure primarily focuses on GFA, which is estimated by one graph convolutional layer followed by two consecutive fully-connected layers.

FIG. 5 is a diagram illustrating an exemplary graph convolutional neural network (GCNN) architecture according to an embodiment of the subject matter described herein. In this example, the numbers of feature maps are set to 64, 128, and 256 for the respective levels. The last graph convolutional layer in the image reconstruction branch has R channels with pre-shuffled feature maps for pixel shuffling. Notably, FIG. 5 illustrates an exemplary block diagram of a GCNN-based reconstruction framework system (e.g., "GCNN 500"). In particular, the reconstruction method of the disclosed subject matter may be logically depicted in FIG. 5. In some embodiments, a GCNN can be utilized to learn the mapping function, since dMRI data are not necessarily Cartesian-sampled in the diffusion wavevector space.

In some embodiments, GCNN 500 can be configured to utilize adversarial learning to generate more realistic image outputs. In adversarial learning, the generator (e.g., GCNN 500) may attempt to produce outputs that cannot be distinguished from the target images by an adversarially trained discriminator. In some embodiments, the training of the generator and the discriminator is performed in an alternating fashion. Here, the generator includes GCNN 500 with two output branches as shown in FIG. 5. One output branch produces the patches for full DW images (e.g., output feature map 508), and another branch produces diffusion index map 510, such as GFA, of the corresponding patches. Notably, two separate discriminators are applied for the predicted DW image and the predicted diffusion index. That is, a discriminator $D_I$ that classifies between the predicted DW image and the real DW image, and another discriminator $D_{GFA}$ that classifies between the predicted GFA image and the real GFA image. Leaky ReLU (LReLU) activation can be used for both discriminators with negative slope 0.2 for stable GANs. For the input source x, the target DW image $y_1$, and the target GFA $y_{GFA}$, the generator loss is defined as the combination of pixel-wise difference, GFA difference, and adversarial loss:

$$\mathcal{L}_G(x, y_I, y_{GFA}) = \lambda_I \|G_I(x) - y_I\|_1 + \lambda_{GFA} \|G_{GFA}(x) - y_{GFA}\|_1 + \lambda_{ADV}(\mathcal{L}_{BCE}(D_I(G_I(x)), 1) + \mathcal{L}_{BCE}(D_{GFA}(G_{GFA}(x)), 1))$$

where $\mathcal{L}_{BCE}$ is the binary cross-entropy function, and $D_I$ and $D_{GFA}$ are the discriminators for the predicted images and GFA, respectively. In this formula above, $G_I(x)$ and $G_{GFA}(x)$ are the outputs of the generator in the image reconstruction branch and diffusion index branch, respectively. The discriminator loss can be defined as:

$$\mathcal{L}_{D_I}(x, y_I) = \mathcal{L}_{BCE}(D_I(y_I), 1) + \mathcal{L}_{BCE}(D_I(G_I(x)), 0)$$
$$\mathcal{L}_{D_{GFA}}(x, y_{GFA}) = \mathcal{L}_{BCE}(D_{GFA}(y_{GFA}), 1) + \mathcal{L}_{BCE}(D_{GFA}(G_{GFA}(x)), 0).$$

$D_I$ comprises of three graph convolutions with 64, 128, 256 features, each followed by LReLU and graph pooling. $D_{GFA}$ includes three fully-connected layers with 64, 32, and 1 node(s), respectively (e.g., see blocks 520-522).

In some embodiments, GCNN 500 is trained from undersampled versions of diffusion magnetic resonance (MR) images to produce full diffusion-weighted volumetric versions of diffusion magnetic resonance images. Once trained, GCNN 500 can take as input an undersampled diffusion magnetic resonance image for which there is no corresponding fully sampled image and produce a reconstructed image that represents a fully sampled diffusion magnetic resonance image (e.g., a full DW volume).

Referring to FIG. 5, for each convolution layer (e.g., see blocks 532-542) included in GCNN 500, K corresponds to a Chebyshev polynomial order and F corresponds to the number of feature maps. In some embodiments, the convolutional block "Conv. Block" (i.e., blocks 532-542) denotes a graph convolutional layer followed by batch normalization and ReLU activation. This is shown in individual block 511. Similarly, "Res. Conv. Block" (e.g., see blocks 551-555; also shown in more detail in block 512) denotes two Conv. Blocks with identity connection in order to mitigate the gradient vanishing problem. "Graph Pool" blocks 571-572 and "Graph Unpool" blocks 573-574 denotes graph coarsening and uncoarsening, respectively. Further, these blocks respectively correspond to pooling and unpooling in standard Cartesian CNN. Upsampling in slice-select direction is implemented by pixel-shuffling, which converts the feature maps 506 in different channels into the output vector (i.e., an output feature map 508) in different spatial locations. Note that the proposed graph convolutional operation is based on Chebyshev polynomial. However, it can be implemented by other kinds of orthogonal polynomials, in general.

In some embodiments, GCNN 500 may include an algorithm and/or type of machine learning system that can be configured with initial training data that may involve two image domains, e.g., fully sampled MRI images and undersampled MRI images. Using the training data and undersampled volumes, the GCNN can learn to better generate/reconstruct a full DW volumetric image to represent data as if it were a full DW volumetric image obtained by conventional means. In some embodiments, GCNN 500 may be trained by training the generator and the discriminator against each other until a predetermined condition is reached (e.g., a particular error rate for the discriminator is reached or a significant number of undersampled DW volumes generated by the generator are representative of the full DW volumes). In some embodiments, a generator may include a convolutional neural network and a discriminator may include a convolutional neural network.

In some embodiments, the GCNN algorithm can be trained to execute an interpolation between two data points. Notably, the algorithm can be trained to study two data points and subsequently derive a reasonable assumption of the two data points. For example, the system can be configured to receive information that corresponds to the collected undersampled image data, which notably requires interpolation in order to recover or generate the data that is lost or missing (as compared to a full DW image scan or volume). Specifically, the undersampled image data can be processed by GCNN 500 to recover the lost data and reconstruct a volumetric image of a subject. In particular, the GCNN system can leverage interpolation of the undersampled data in order to derive a volumetric image that is associated with a higher level of accuracy.

At present, diffusion MRI (dMRI) typically requires a lengthy acquisition time for probing water diffusion in various directions and scales. In the present disclosure, it is proposed to accelerate the acquisition via slice-interleaved diffusion encoding (SIDE), where only a subsample of slices are acquired for each diffusion wavevector, and demonstrate that it is possible to reconstruct the full diffusion-weighted volumes from highly slice-undersampled volumes using GCNN 500.

In one example procedure, dMRI data was acquired from seven healthy subjects (after obtaining informed consent) using a protocol approved by the institute and a 3T Siemens whole-body Prisma scanner (note: Siemens Healthcare, Erlangen, Germany). Diffusion imaging was performed with a monopolar diffusion-weighted SE-EPI sequence. The SMS radio frequency (RF) excitation with controlled aliasing (e.g., blipped-CAIPI) was employed to reduce the penalty of geometry factor (i.e., the "g-factor"). The SMS factor is 5. In some embodiments, imaging parameters were as follows: resolution =1.5 mm isotropic; FOV=192×192×150 mm$^3$; image dimensions=128×128×100; partial Fourier=⅝; no in-plane acceleration was used; bandwidth=1776 Hz/Px; 160 wavevectors distributed over the 4 b-shells of b=500; 1000; 2000 and 3000 s/mm$^2$, plus one b=0; TR/TE=$^{312}$⁄₉₀ ms; 32-channel head array coil. The total acquisition time is 8.32 minutes for each phase-encoding direction. Note that $N_d$=160 and $N_9$=$^{10}$%=20.

The outcome of one example procedure indicated positive results. Notably, the method was evaluated under various acceleration factors R=2; 4; 10 for 48 DW images b=2000 s/mm$^2$. For R=2, the 1st to 10th cycles were selected from 20 cycles. For R=4, the 1st, 3rd, 5th, 7th, and 9th cycles were selected. For R=10, we selected the 1st and 16th cycles. Training was carried out using 5×5×1×48 input patches and 5×5×R×48 output patches. The numbers of subjects for training, validation, and testing were 4, 1, and 2, respectively.

Figure 6:
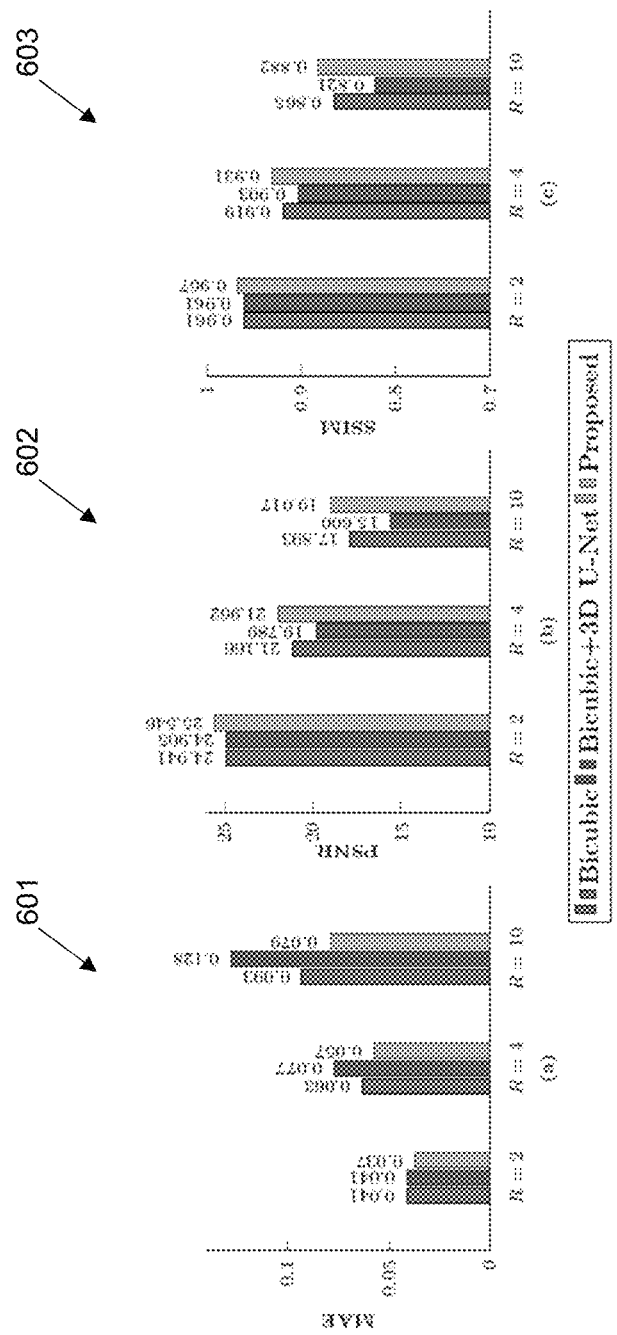
FIG. 6 is a graphical representation of an exemplary quantitative comparison of produced images according to an embodiment of the subject matter described herein.

The disclosed method was compared with bicubic interpolation and 3D U-Net applied to the input upsampled by bicubic interpolation. The quantitative results are summarized in graphs 601-603 as shown in FIG. 6. Notably, FIG. 6 is a graphical representation of an exemplary quantitative comparison of produced images according to an embodiment of the subject matter described herein.

Figure 7:
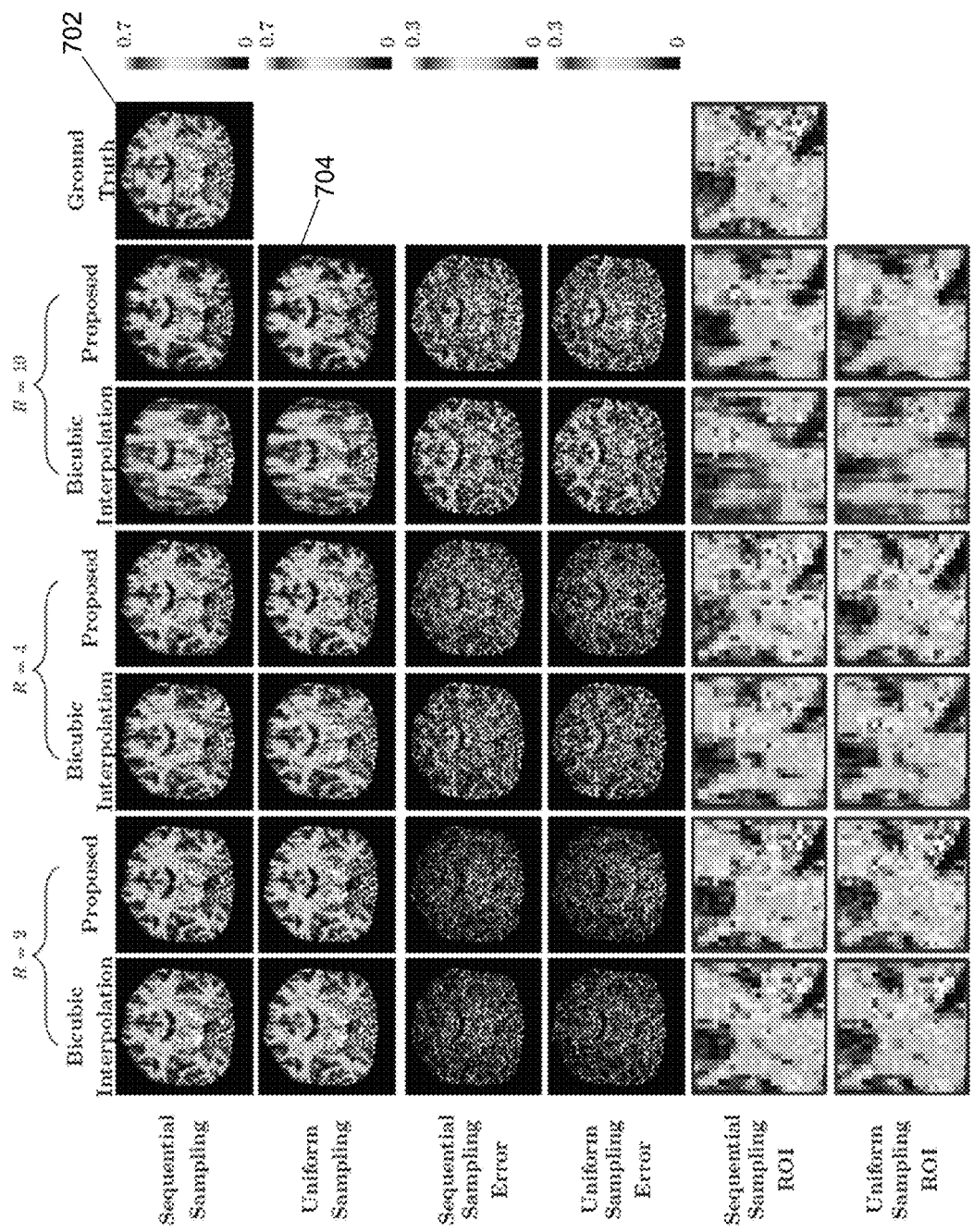
FIG. 7 is a diagram illustrating full views and close-up views of predicted Generalized Fractional Anisotropy (GFA) images and corresponding error maps according to an embodiment of the subject matter described herein.

FIG. 7 is a diagram illustrating full views and close-up views of predicted Generalized Fractional Anisotropy (GFA) images and corresponding error maps according to an embodiment of the subject matter described herein. The representative GFA image results in FIG. 7 indicate that the disclosed method recovers more structural details even for high acceleration factors. Note that the input data is not exactly equally-spaced slices. In some examples, GFA results are also compared with retrospective slice-undersampling for equally-spaced data. Notably, FIG. 7 depicts full views and close-up views of the predicted GFA images and the corresponding error maps. FIG. 7 further shows sequential sampling that includes sampling from selective cycles. Likewise, the uniform sampling is shown to include retrospective undersampling. Further, the disclosed system can compare a uniform sampling image 704 and a ground truth image 702 shown in FIG. 7 to assess the accuracy (e.g., omission of artifacts) of the final uniform sampling image 704. As used herein, ground truth image can be generated when you receive and/or obtain the full volumetric image data. Moreover, the closer the ground truth image 702 and the sampling image resemble each other, the less likely an artifact was introduced.

Figure 8:
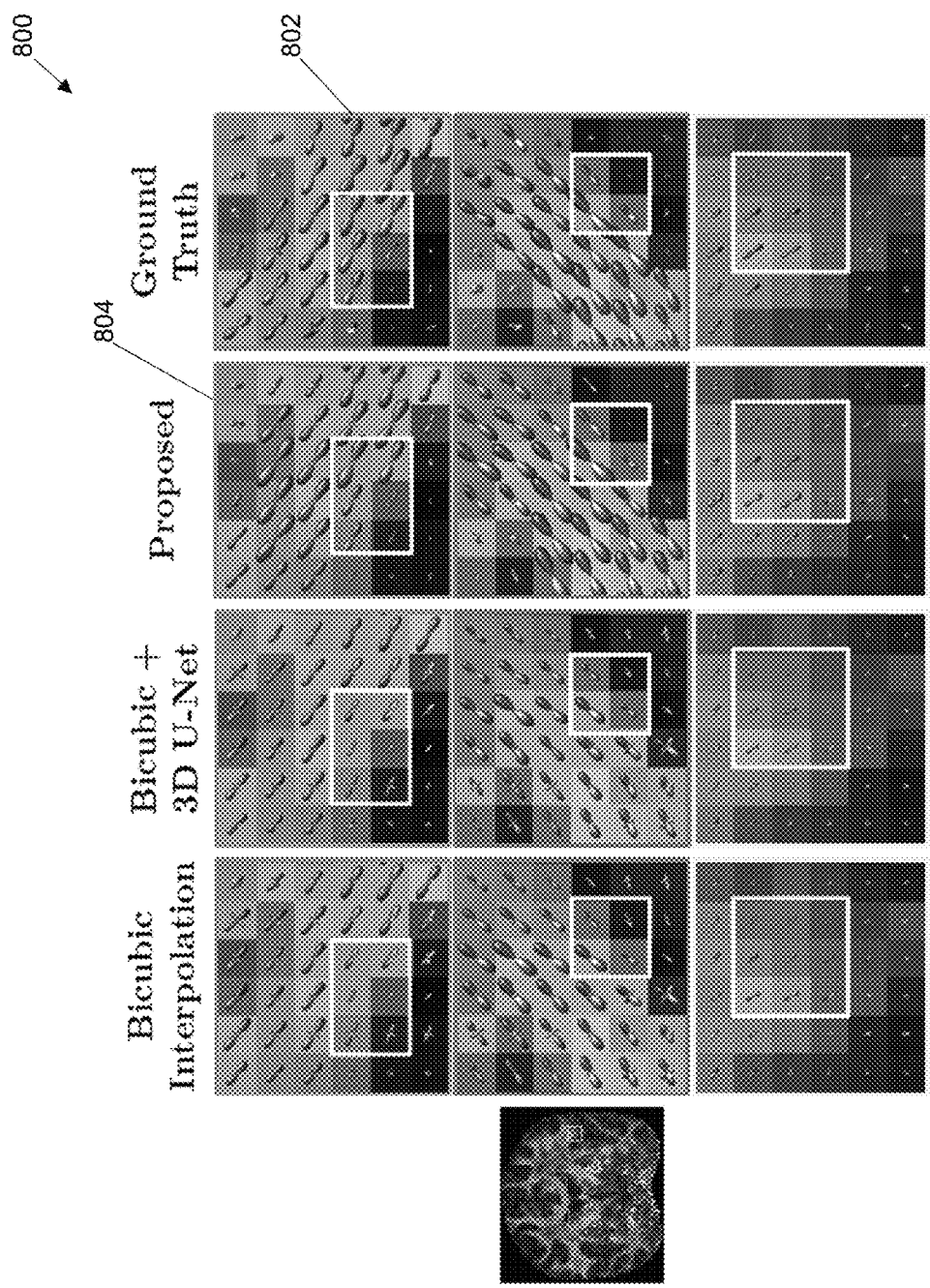
FIG. 8 is a diagram illustrating exemplary views of representative fiber Orientation Distribution Functions (ODFs) according to an embodiment of the subject matter described herein.

FIG. 8 is a diagram illustrating exemplary views of representative fiber Orientation Distribution Functions (ODFs) according to an embodiment of the subject matter described herein. In some embodiments, fiber ODFs are generated by employing CSD implemented MRtrix3 with the default setting. FIG. 8 shows that the disclosed method can yield fiber orientation distribution functions (i.e., proposed/produced image 804) that are closer to the ground truth image 802 with less partial volumetric image effects. For example, FIG. 8 depicts representative fiber ODFs associated with R=4.

Figure 9:
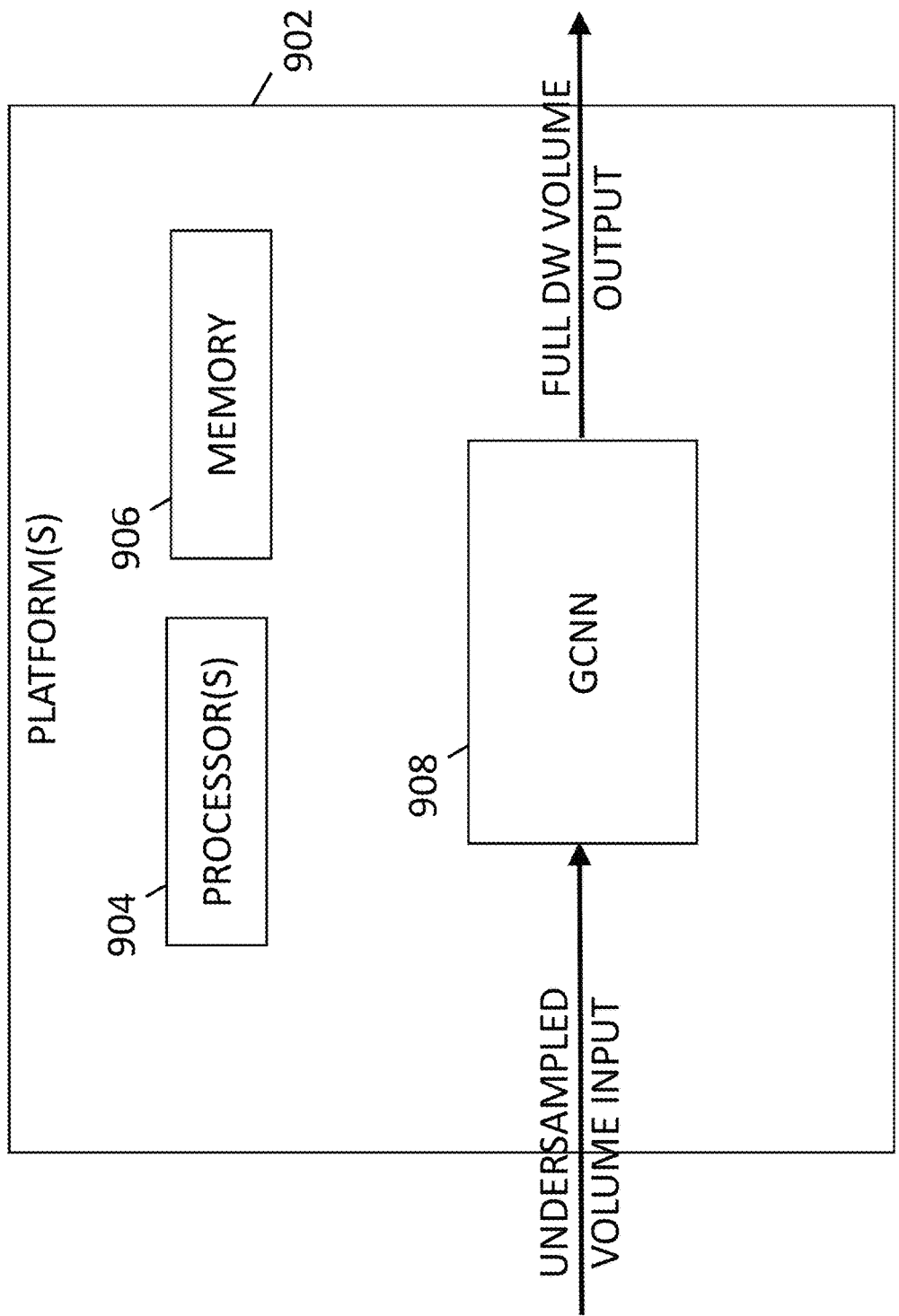
FIG. 9 is a block diagram of an example system for accelerating diffusion magnetic resonance imaging acquisition via slice interleaved diffusion encoding according to an embodiment of the subject matter described herein.

FIG. 9 is a block diagram of an example system 900 for accelerating diffusion magnetic resonance imaging acquisition via slice interleaved diffusion encoding. In FIG. 9, system 900 may include one or more computing platform(s) 902 having one or more processor(s) 904 and memory 906. A GCNN 908 may reside on computing platform(s) 902 and be executable by processor(s) 904. GCNN 908 may receive slice-undersampled diffusion weighted volumes as input and may generate a full diffusion-weighted (DW) volumetric image as output. In some embodiments, GCNN 908 may represent a network that is trained using one or more aspects described herein.

In some embodiments, computing platform(s) 902 with GCNN 908 may be located in a cloud network. In such embodiments, cloud-based GCNN 908 may receive slice-undersampled diffusion weighted volumes from an on-premises network of a user and may provide, as output, a full diffusion-weighted volume.

In some embodiments, computing platform(s) 902 with GCNN 908 may be located in an on-premises or local network of a user. In such embodiments, GCNN 908 may receive slice-undersampled diffusion weighted volumes from an on-premises network of a user and may provide, as output, a full diffusion-weighted volume.

It will be appreciated that FIG. 9 is for illustrative purposes and that various entities, their locations, and/or their functions may be changed, altered, added, or removed. For example, some entities and/or functions may be combined into a single entity. In another example, an entity and/or function may be located at or implemented by two or more entities.

Figure 10:
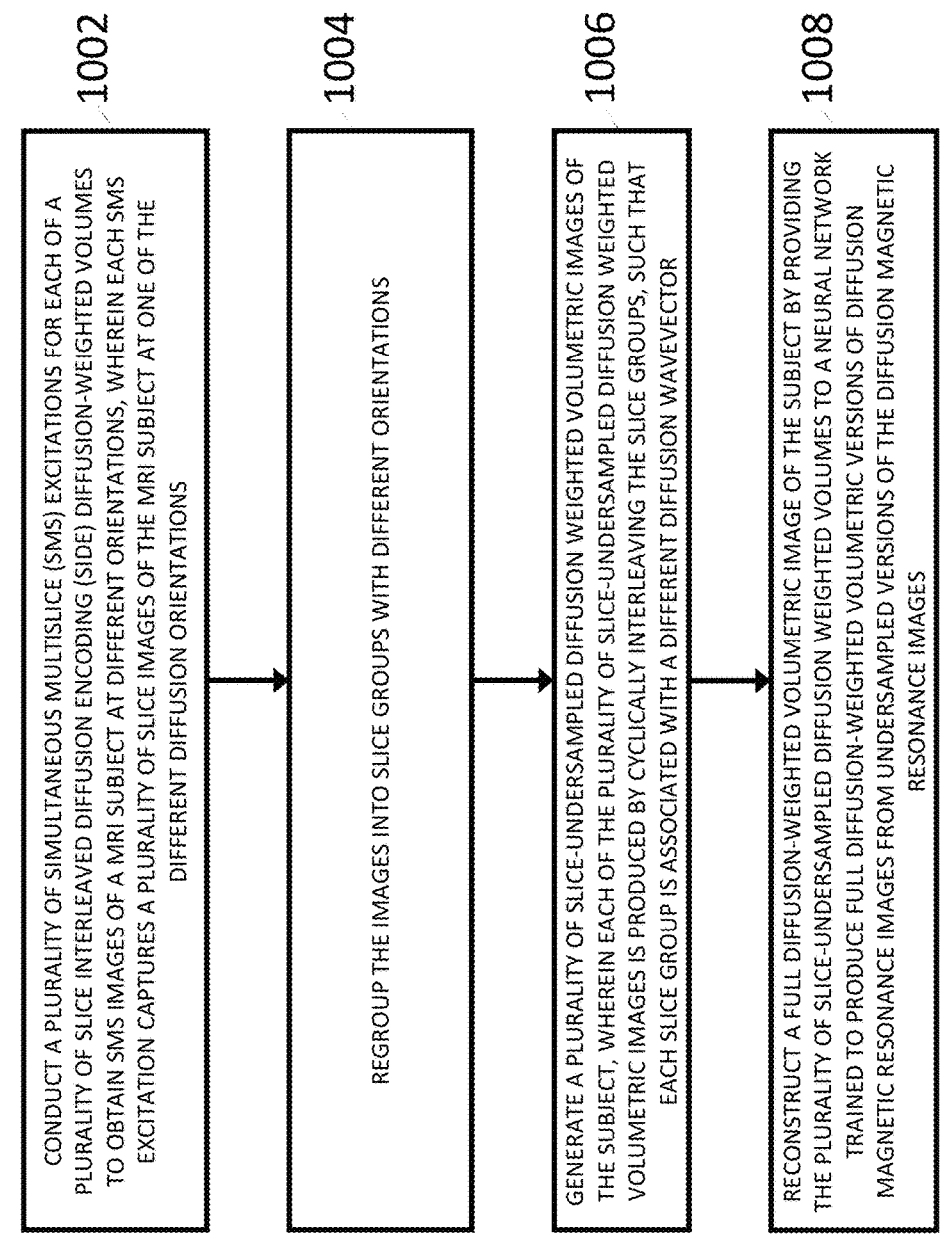
FIG. 10 is a flow chart illustrating an example process for accelerating diffusion magnetic resonance imaging acquisition via slice interleaved diffusion encoding according to an embodiment of the subject matter described herein.

FIG. 10 is a flow chart illustrating an example process for accelerating dMRI acquisition via SIDE. In some embodiments, process 1000 described herein, or portions thereof, may be performed at or by GCNN 500, computing platform(s) 902, GCNN 908, and/or another module or device. For example, computing platform(s) 902 may include a mobile device, a computer, or other equipment (e.g., a medical device) and GCNN 908 may include various deep learning based algorithms executing on computing platform(s) 902 for transforming or translating input (e.g., slice-undersampled diffusion weighted volumes) into output (e.g., a full DW volume). In some embodiments, process 1000 may include steps 1002-1006.

In step 1002, plurality of excitations are conducted to SMS images of an MRI subject at different diffusion gradient orientations in a single image volume, wherein each of the excitations is sensitized to a certain gradient orientation. In some embodiments, the method includes conducting a plurality of simultaneous multislice (SMS) excitations for each of a plurality of SIDE diffusion-weighted volumes to obtain SMS images of an MRI subject at different diffusion orientations, wherein each SMS excitation captures a plurality of slice images of the subject at one of the different diffusion orientations. For example, this step can be described as the acquiring of SIDE volumes (e.g., each volume corresponding to multiple diffusion orientations).

In some embodiments, the different diffusion orientations of the plurality of excitations are designated using different diffusion wavevectors.

In step 1004, the images are regrouped into slice groups with different orientations.

In step 1006, a plurality of slice-undersampled diffusion weighted volumetric images of the subject is generated. In some embodiments, each of the plurality of slice-undersampled diffusion weighted volumetric images is produced by cyclically interleaving the slice groups, such that each slice group is associated with a different diffusion wavevector. For example, the slices in the SIDE volumes are reorganized into multiple slice-undersampled volumes (e.g., each volume corresponding to one diffusion orientation).

In some embodiments, each of the plurality of excitations is an SMS excitation that is processed for a period of time equal to a predefined repetition time (TR).

In some embodiments, the cyclically interleaving includes offsetting the diffusion wavevectors that sequentially encode the slice groups by an integer factor.

In some embodiments, the slice groups remain in a same sequence in each encoding cycle and are encoded by the offset diffusion wavevectors in each subsequent encoding cycle.

In step 1008, full diffusion-weighted volumetric images of the subject are reconstructed by providing the plurality of slice-undersampled diffusion weighted volumes to a neural network trained to produce full diffusion-weighted volumetric versions of diffusion magnetic resonance images from undersampled versions of the diffusion magnetic resonance images. For example, full volumes can be reconstructed (i.e., where each volume corresponds to one diffusion orientation).

In some embodiments, each SIDE diffusion-weighted volumetric image contains information resulting from the different orientations.

In some embodiments, the GCNN is configured to utilize interpolation algorithms to reconstruct the full diffusion-weighted volume It will be appreciated that process 1000 is for illustrative purposes and that different and/or additional actions may be used. It will also be appreciated that various actions described herein may occur in a different order or sequence.

The disclosed subject matter demonstrates that the acquisition of dMRI data can be effectively accelerated by slice-undersampling. Notably, full diffusion-weighted images can be reconstructed via the disclosed GCNN (see FIGS. 5 and 9), which jointly considers spatio-angular information. Experimental results show that the disclosed method can achieve an acceleration factor as high as 50 with the assistance of multiband imaging.

In some embodiments, an alternative reconstruction scheme for diffusion MRI data acquired using SIDE can be utilized by the disclosed subject matter. As indicated above, dMRI offers a unique probe into white matter pathways in the living human brain in association with development and disorders in a non-invasive manner. However, dMRI is characterized by long acquisition times due to the need to acquire a large number of DW images with different diffusion encodings for sufficient coverage of the q-space over a range of diffusion gradient directions. Speeding up dMRI acquisition is needed to reduce motion artifacts, patient discomfort, and imaging costs.

Acceleration of dMRI acquisition typically involves a sampling scheme and a reconstruction strategy. In contrast to the conventional approaches of acquiring a full DW volume for each diffusion wavevector, SIDE acquires for each TR a volume comprising interleaved slice groups, each corresponding to a different diffusion wavevector. This reconstruction technique allows SIDE to rapidly acquire information associated with a large number of wavevectors within a short period of time. Accordingly, a reconstruction method that utilizes SIDE can be configured to not rely on training data. For example, when combined with multi-band imaging, the disclosed method is capable of reducing the amount of data that needs to be acquired by as much as 25 times, therefore significantly speeding up acquisition and making high angular resolution diffusion imaging much more feasible, particularly for pediatric, elderly, and claustrophobic patients. Notably, the inverse problem involved in recovering the full DW images can be formulated as a constrained variational problem regularized by multidimensional total variation. As such, the problem may be solved efficiently by the disclosed subject matter via the use of alternating direction method of multipliers (ADMM). Experimental results based on SIDE data of adults indicate that DW images can be recovered with high fidelity despite high undersampling for multifold acceleration.

In some embodiments, SIDE accelerates acquisition of DW images. As indicated above, SIDE involves SMS excitation 1102 of a slice group (SG), where $N_g$ denotes the number of slice groups in a volume and $N_d$ denotes the total number of wavevectors. In conventional acquisition schemes, all slice groups in a volume share the same diffusion encoding. In SIDE, each slice group is associated with a different diffusion wavevector. Each SIDE cycle covers every wavevector with a slice group, amounting to acquiring $N_d/N_g$ volumes in $N_d/N_g$ TRs. In some embodiments, $N_d$ is a multiple of $N_g$. With each transition to the next cycle, the wavevector table is offset by some integer, such as "1". Further, $N_g$ cycles cover all the slices of all diffusion wavevectors. A subset of the cycles can be selectively acquired to achieve a certain acceleration factor R. Sorting the slice groups in the SIDE volumes according to their associated wavevectors provides $N_d$ volumes with subsampled slices. An illustration of SIDE acquisition is presented in FIG. 11 for $N_d=16$ and $N_d/N_g=4$. When the acceleration factor is R=2, only half of the cycles need to be acquired.

Figure 11:
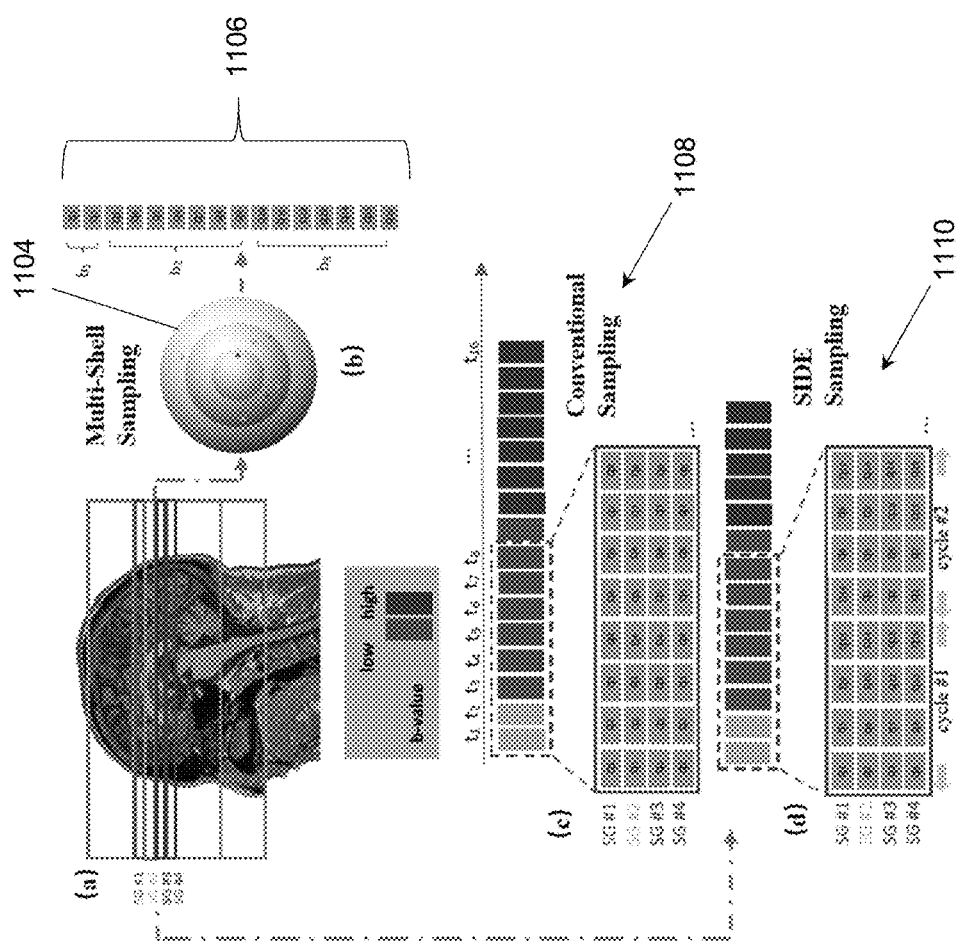
FIG. 11 is a diagram representing an alternate slice-interleaved diffusion encoding (SIDE) acquisition scheme according to an embodiment of the subject matter described herein.

In some embodiments, multi-shell sampling 1104 may be conducted with 16 diffusion vectors (e.g., see wavevectors 1106) covering 3 shells as shown in FIG. 11. After multi-shell sampling is conducted the SMS slice groups are subjected to one-volume-one-encoding sampling 1108 in each volume associated with the same diffusion encode. Afterwards, SIDE acquisition with SMS slice groups in each volume associated with different wavevectors is conducted (e.g., see block 1110).

After the DW acquisition phase is completed, the reconstruction scheme can be initiated by the disclosed subject matter. In some example, the DW images can be reshaped into a matrix $X \in \mathbb{R}^{N_v \times N_s}$, and $N_v$ is the number of voxels in each DW image and $N_v=N_xN_yN_z$ where $N_x$, $N_y$, and $N_z$ are the image dimensions in the x, y, and z directions, respectively. Further, $N_d$ is equal to the number of wavevectors. Afterwards, a set of SIDE image volumes $\{X_k^S\}_{k=1}^{N_d}$ can be represented as:

$$X_k^S(:,l) = H_l X q_{kl} + n_{kl}$$

where $X_k^S(:,l)$ is the l-th column vector of $X_k^s$ and represents the l-th observed slice along the z-direction, k is the volume index, and $n_{kl}$ is the measurement noise. Matrix $H_l$ is a slice selector along the z direction and vector $q_{dl}$ is a gradient selector. $X_k^S$ is a partial volume that does not cover all the slices due to subsampling by a factor of R.

In some embodiments, one goal is to reconstruct the full volumes X from the subsampled DW images. One way to obtain X is to solve:

$$\min_X \frac{1}{2} \sum_{k,l} \|H_l X q_{kl} - X_k^S(:,l)\|_F^2$$

However, the inverse problem is ill-posed and can be regularized spatially by using the total variation (TV) semi-norm of X, giving $$\min_X \frac{1}{2} \sum_{k,l} \|H_l X q_{kl} - X_k^S(:,l)\|_F^2 + \lambda \|X\|_{TV}$$

Notably, parameter $\lambda$ is nonnegative and controls the tradeoff between data fidelity and the degree of regularization. For angular regularization, X is represented as real and symmetric spherical harmonics (SH) of maximum order $l_{max}=8$ via $X=AV$, where A is a matrix of the SH basis functions and V is the corresponding SH coefficients. Therefore, $$\min_X \frac{1}{2} \sum_{k,l} \|H_l X q_{kl} - X_k^S(:,l)\|_F^2 + \lambda \|X\|_{TV} \text{ s.t. } X=AV$$

It is further submitted that the disclosed subject matter affords a method of optimization. Specifically, the alternating direction method of multipliers (ADMM) can be utilized for solving the preceding equation, which involves highdimensional variables and non-differentiable convex optimization. To regularize the ill-posed problem, the TV norm utilized includes:

$$\sum_{k=1}^{N_d} \|X_{(k)}\|_{TV}$$

where $X_{(k)}$ is the k-th row of X reshaped into a tensor of size $N_x \times N_y \times N_z$. The TV regularization term encourages X to be spatially smooth. Thus, $\|\cdot\|_{TV}$ can be the anisotropic or isotropic TV norm.

ADMM decomposes a large global problem into a series of smaller local subproblems, and attempts to combine the benefits of augmented Lagrangian methods and dual decomposition for constrained optimization problems. The constrained optimization problem can be reformulated as the following unconstrained optimization problem:

$$L(X, V, Y_{\{1,\ldots,N_d\}}, \Psi_{\{1,\ldots,N_d\}}\Phi) =$$

$$\min_X \frac{1}{2}\sum_{k,l} \|H_l X q_{kl} - X_k^S(:,l)\|_F^2 + \lambda\sum_{k=1}^{N_d}\|Y_k\|_{TV} + \sum_{k=1}^{N_d}\langle \Psi_k, Y_k - X_{(k)}\rangle +$$

$$\frac{\rho_1}{2}\sum_{k=1}^{N_d}\|Y_k - X_{(k)}\|_F^2 + \langle \Phi, X - AV\rangle + \frac{\rho_2}{2}\|X - AV\|_F^2,$$

where $(\cdot, \cdot)$ denotes the Frobenius inner product. Applying ADMM, the following steps are carried out to minimize $L(X,V,Y_{\{1,\ldots,N_d\}}, \Psi_{\{1,\ldots,N_d\}}, \Phi)$ over X, V, and auxiliary variables $Y_{\{1,\ldots,N_d\}}$, and update Lagrangian multipliers $\Psi_{\{1,\ldots,N_d\}}$ and $\Phi$ in each iteration t:

Subproblem 1—Update V by minimizing $$V^{(t+1)} = \arg\min_V \frac{\rho_2}{2}\|X^{(t)} - AV + \Phi^{(t)}\|_2^2.$$

Subproblem 2—Update $Y_{1,\ldots,N_d}$ by minimizing $$Y_k^{(t+1)} = \arg\min_{Y_i} \rho_1\sum_{k=1}^{N_d}\|Y_k - X_{(k)}^{(t)} + \Psi_k^{(t)}\|_2^2 + \lambda\sum_{k=1}^{N_d}\|Y_k\|_{TV}.$$

Subproblem 3—Update X by minimizing $$X^{(t+1)} = \arg\min_X \frac{1}{2}\sum_{k,l}\|H_l X q_{kl} - X_k^S(:,l)\|_F^2 +$$

$$\frac{\rho_1}{2}\sum_{k=1}^{N_d}\|Y_k^{(t+1)} - X_{(k)} + \Psi_k^{(t)}\|_F^2 + \frac{\rho_2}{2}\|X - AV^{(t+1)} + \Phi^{(t)}\|_F^2.$$

Subproblem 4—Update $\Psi$ and $\Phi$ by $$\Psi_k^{(t+1)} = \Psi_k^{(t)} + (Y_k^{(t+1)} - X_{(k)}^{(t+1)}),$$

$$\Phi^{(t+1)} = \Phi^{(t)} + (X^{(t+1)} - AV^{(t+1)}).$$

Utilizing the aforementioned reconstruction technique, the disclosed subject matter enables dMRI acquisition to be significantly accelerated when combined with SIDE acquisition. Notably, experimental results show that some embodiments of the method can yield an acceleration factor as high as 25 folds when combined with SMS imaging, allowing more than one hundred DW images (e.g., 1.5 mm isotropic resolution) to be acquired within a couple of minutes. Accordingly, the disclosed subject matter demonstrates a reconstruction method that affords a notable technical improvement with regard to both the efficiency and speed of dMRI acquisition techniques.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for accelerating diffusion magnetic resonance imaging (MRI) acquisition via slice interleaved diffusion encoding (SIDE), the method comprising:
   conducting a plurality of simultaneous multislice (SMS) excitations for each of a plurality of SIDE diffusion-weighted volumes to obtain SMS images of an MRI subject at different diffusion orientations, wherein each SMS excitation captures a plurality of slice images of the MRI subject at one of the different diffusion orientations;
   regrouping the images into slice groups with different orientations;
   generating a plurality of slice-undersampled diffusion weighted volumetric images of the MRI subject, wherein each of the plurality of slice-undersampled diffusion weighted volumetric images is produced by cyclically interleaving the slice groups, such that each slice group is associated with a different diffusion wavevector; and
   reconstructing full diffusion-weighted volumetric images of the MRI subject by providing the plurality of slice-undersampled diffusion weighted volumetric images to a neural network trained to produce full diffusion-weighted volumetric versions of diffusion magnetic resonance images from undersampled versions of the diffusion magnetic resonance images.

2. A system for accelerating diffusion magnetic resonance imaging (MRI) acquisition via slice interleaved diffusion encoding (SIDE), the system comprising:
   at least one computing platform including at least one processor; and
   a diffusion MRI acquisition acceleration engine executable by the at least one processor for:
   conducting a plurality of simultaneous multislice (SMS) excitations for each of a plurality of SIDE diffusion-weighted volumes to obtain SMS images of an MRI subject at different diffusion orientations, wherein each SMS excitation captures a plurality of slice images of the MRI subject at one of the different diffusion orientations;
   regrouping the images into slice groups with different orientations;
   generating a plurality of slice-undersampled diffusion weighted volumetric images of the MRI subject, wherein each of the plurality of slice-undersampled diffusion weighted volumetric images is produced by cyclically interleaving the slice groups, such that each slice group is associated with a different diffusion wavevector; and
   reconstructing full diffusion-weighted volumetric images of the MRI subject by providing the plurality of slice-undersampled diffusion weighted volumetric images to a neural network trained to produce full diffusion-weighted volumetric versions of diffusion magnetic resonance images from undersampled versions of the diffusion magnetic resonance images.

3. A non-transitory computer readable medium having stored thereon executable instructions that when executed by at least one processor of at least computer cause the at least one computer to perform steps comprising:
conducting a plurality of simultaneous multislice (SMS) excitations for each of a plurality of slice interleaved diffusion encoding (SIDE) diffusion-weighted volumes to obtain SMS images of an MRI subject at different orientations, wherein each SMS excitation captures a plurality of slice images of the MRI subject at one of the different diffusion orientations;
regrouping the images into slice groups with different orientations;
generating a plurality of slice-undersampled diffusion weighted volumetric images of the MRI subject, wherein each of the plurality of slice-undersampled diffusion weighted volumetric images is produced by cyclically interleaving the slice groups, such that each slice group is associated with a different diffusion wavevector; and
reconstructing full diffusion-weighted volumetric images of the MRI subject by providing the plurality of slice-undersampled diffusion weighted volumetric images to a neural network trained to produce full diffusion-weighted volumetric versions of diffusion magnetic resonance images from undersampled versions of the diffusion magnetic resonance images.

4. The method of claim 1 wherein the plurality of SMS excitations is processed for a period of time equal to a predefined repetition time (TR).

5. The method of claim 1 wherein cyclically interleaving includes offsetting diffusion wavevectors that sequentially encode the slice groups by an integer factor.

6. The method of claim 5 wherein the slice groups remain in a same sequence in each encoding cycle and are encoded by the offset diffusion wavevectors in each subsequent encoding cycle.

7. The method of claim 1 wherein the different orientations of the plurality of SMS excitations are designated using different diffusion wavevectors.

8. The method of claim 1 wherein each of the SIDE diffusion-weighted volumes contains information resulting from the different diffusion orientations.

9. The method of claim 1 wherein the neural network is configured to utilize interpolation algorithms to reconstruct the full diffusion-weighted volumetric images.

10. The system of claim 2 wherein each of the plurality of slice-undersampled diffusion weighted volumes is processed for a period of time equal to a predefined repetition time (TR).

11. The system of claim 2 wherein cyclically interleaving includes offsetting diffusion wavevectors that sequentially encode the slice groups by an integer factor.

12. The system of claim 11 wherein the slice groups remain in a same sequence in each encoding cycle and are encoded by the offset diffusion wavevectors in each subsequent encoding cycle.

13. The system of claim 2 wherein the different orientations of the plurality of SMS excitations are designated using different diffusion wavevectors.

14. The system of claim 2 wherein each of the SIDE diffusion-weighted volumes contains information resulting from the different orientations.

15. The system of claim 2 wherein the neural network is configured to utilize interpolation algorithms to reconstruct the full diffusion-weighted volumetric image.

16. The non-transitory computer readable medium of claim 15 wherein each of the plurality of SMS excitations is processed for a period of time equal to a predefined repetition time (TR).

17. The non-transitory computer readable medium of claim 15 wherein cyclically interleaving includes offsetting diffusion wavevectors that sequentially encode the slice groups by an integer factor.

18. The non-transitory computer readable medium of claim 17 wherein the slice groups remain in a same sequence in each encoding cycle and are encoded by the offset diffusion wavevectors in each subsequent encoding cycle.

19. The non-transitory computer readable medium of claim 15 wherein the different orientations of the plurality of SMS excitations are designated using different diffusion wavevectors.

20. The non-transitory computer readable medium of claim 15 wherein each of the SIDE diffusion-weighted volumes contains information resulting from the different orientations.

* * * * *